(12) United States Patent
Ettema et al.

(10) Patent No.: US 6,828,339 B2
(45) Date of Patent: Dec. 7, 2004

(54) AMLODIPINE SALT FORMS AND PROCESSES FOR PREPARING THEM

(75) Inventors: Gerrit J. B. Ettema, Nijmegen (NL); Hans Hoorn, Nijmegen (NL); Jacobus M. Lemmens, Nijmegen (NL)

(73) Assignee: Synthon BV, Nijmegen (NL)

(*) Notice: Subject to any disclaimer, the term of this patent is extended or adjusted under 35 U.S.C. 154(b) by 0 days.

(21) Appl. No.: 10/300,003

(22) Filed: Nov. 20, 2002

(65) Prior Publication Data

US 2003/0139455 A1 Jul. 24, 2003

Related U.S. Application Data

(60) Provisional application No. 60/331,742, filed on Nov. 21, 2001.

(51) Int. Cl.[7] ..................... A61K 31/44; C07D 213/803
(52) U.S. Cl. ....................................... 514/356; 546/321
(58) Field of Search ........................... 546/321; 514/356

(56) References Cited

U.S. PATENT DOCUMENTS 4,879,303 A * 11/1989 Davison et al. ............. 514/356

FOREIGN PATENT DOCUMENTS

WO          99/52873    * 10/1999
WO    WO 03/101965        12/2003

OTHER PUBLICATIONS

J. Rollinger, Doctoral Thesis "Polymorphism in Binary Systems—with special regard to antihypertensive drug substances," 1999, University of Innsbruck, Innsbruck, Austria.

J. Rollinger and A. Burger, "Physico–Chemical Characterization of Hydrated and Anhydrous Crystal Forms of Amlodipine Besylate," J. Thermal Analysis and Calorimetry, vol. 68, 2002, pp 361–372.

* cited by examiner

*Primary Examiner*—Rita Desai
(74) *Attorney, Agent, or Firm*—Mark R. Buscher

(57) ABSTRACT

Amlodipine besylate forms are described, including amlodipine besylate hydrates and novel amlodipine besylate anhydrates. A method of making various amlodipine besylate forms from an aqueous medium as well as the use of the same as a calcium channel blocker are described.

15 Claims, 11 Drawing Sheets

AMLODIPINE SALT FORMS AND PROCESSES FOR PREPARING THEM

This application claims the benefit of priority under 35 U.S.C.§119(e) from prior U.S. provisional application No. 60/331,742, filed Nov. 21, 2001, the entire contents of which are incorporated herein by reference.

BACKGROUND OF THE INVENTION

The present invention relates to amlodipine salt forms, including hydrate and anhydrate forms, and to processes for making amlodipine salt forms.

Pharmaceutical products with antianginal and antihypertensive properties are described in U.S. Pat. No. 4,572,909. An especially important compound among those disclosed is amlodipine, ±2-[(2-aminoethoxy)methyl]-4-(2-chlorophenyl)-1,4-dihydro-6-methyl-3,5-pyridinedicarboxylic acid 3-ethyl 5-methyl ester. Amlodipine has the following structural formula.

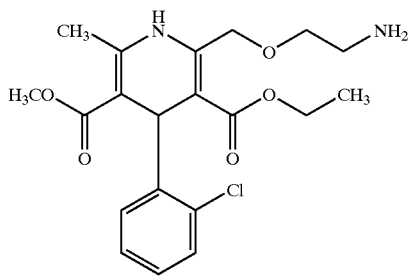

This compound is used for the preparation of a medicament having calcium channel blocking activity that is useful, inter alia, in the management of hypertension, congestive heart failure and angina pectoris. The commercial product of amlodipine (NORVASCO® by Pfizer, Inc.) contains amlodipine besylate, which is described in U.S. Pat. No. 4,879, 303 and corresponding EP 244 944. This patent discloses a single form of amlodipine besylate, namely a crystalline anhydrous besylate salt of amlodipine. This salt form is described as being non-hygroscopic; e.g., it does not form a hydrate. It is formed in the examples by combining either benzene sulphonic acid or ammonium benzenesulphonate with a slurry of amlodipine free base in industrial methylated spirits.

While the amlodipine salt form disclosed in U.S. Pat. No. 4,879,303 is suitable for a commercial product, it would be desirable to find other suitable salt forms of amlodipine. Further, it would be desirable to provide a process for making amlodipine besylate from an aqueous media instead of an organic solvent/slurry.

SUMMARY OF THE INVENTION

The present invention relates to salt forms of amlodipine. A first aspect of the invention relates to amlodipine besylate hydrates. Particular hydrate forms include monohydrate and dihydrate forms, but is not limited thereto.

Another aspect of the invention relates to amlodipine besylate anhydrates that differ from the known, commercially sold anhydrous amlodipine besylate as described in U.S. Pat. No. 4,879,303. In particular, anhydrous forms that do not exhibit a first melting point within the range of 201° C. to 205° C., unlike the known anhydrous form, are preferred.

Still another aspect of the present invention relates to an amorphous amlodipine besylate form and to pharmaceutical compositions containing the same.

A further aspect of the present invention relates to a crystalline pharmaceutical substance comprising a repeating lattice structure formed of the following molecules: (a) amlodipine, an ion thereof, or both; (b) benzene sulfonic acid, an ion thereof, or both; and (c) water.

The above novel compounds/substances of amlodipine can be used in pharmaceutical compositions generally in combination with at least one pharmaceutically acceptable excipient.

Another aspect of the present invention relates to an amlodipine besylate composition that contains at least one amlodipine besylate anhydrate and at least one amlodipine besylate hydrate. Such a composition may further contain a pharmaceutically acceptable excipient and, in such an embodiment, preferably contains the anhydrate and/or hydrate salts in a pharmaceutically effective amount. Similarly, the above novel compounds or a combination thereof, can be used to treat hypertension or angina in mammals by administering an effective amount of the amlodipine compound, e.g. amlodipine besylate hydrate, amlodipine besylate anhydrate, mixtures thereof, etc., to a mammal in need thereof.

Yet another aspect of the present invention relates to a process for forming an amlodipine besylate from an aqueous medium. In particular, the process comprises precipitating an amlodipine besylate from an aqueous solution. The formed solid salt can be a hydrate or anhydrate depending on the conditions employed.

DETAILED DESCRIPTION OF THE INVENTION

Figure 1:
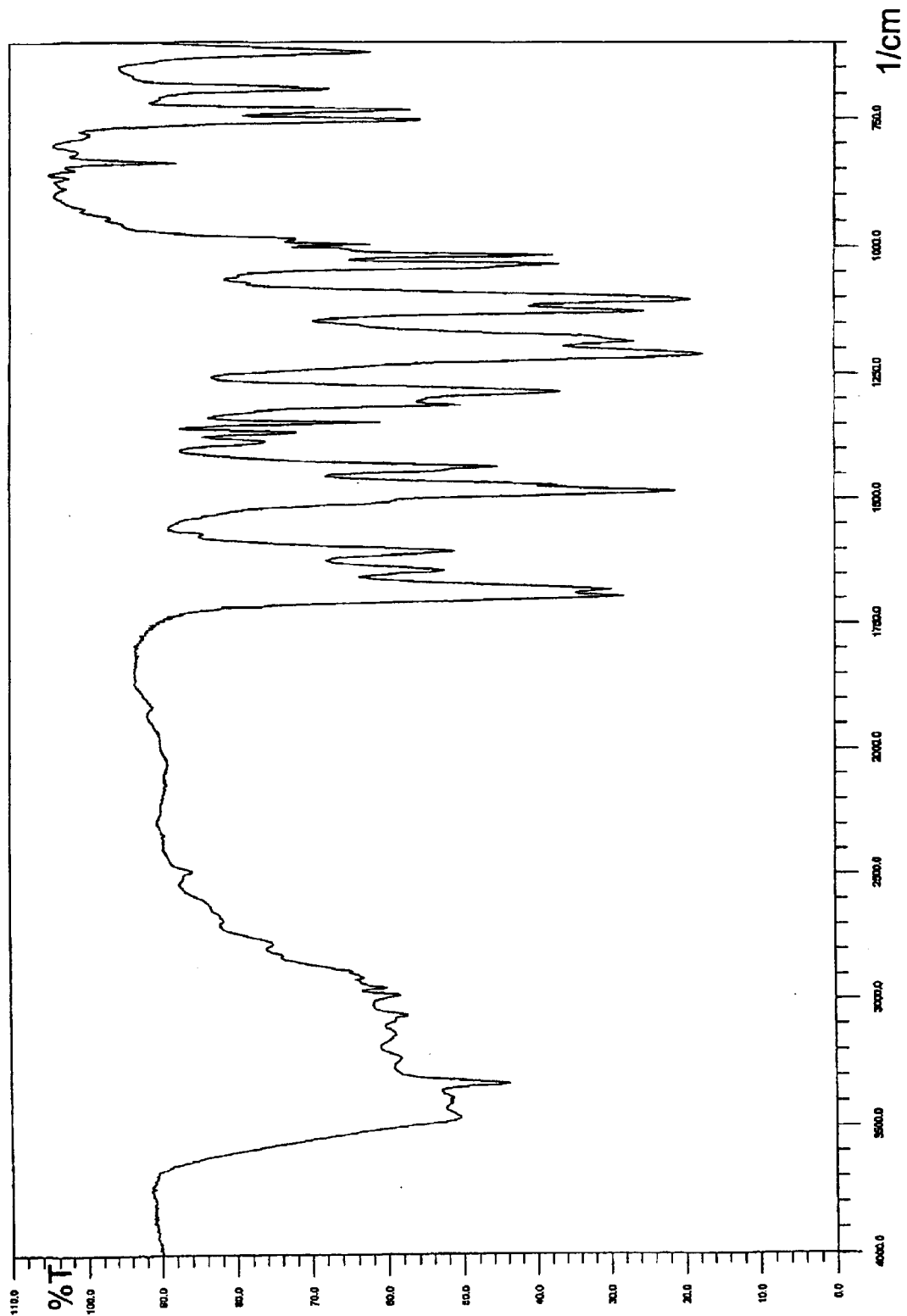
FIG. 1 shows an IR spectrum for the dihydrate salt of example 1(a).

The present invention is based on the discovery that additional forms of amlodipine besylate exist beyond the single known form of the prior art. The invention also relates to a novel process for making various amlodipine besylate forms. The novel amlodipine besylate forms include crystalline hydrates and anhydrates as well as amorphous forms. The hydrate forms include any crystalline amlodipine besylate that contains bound water. Typically the amount of water ranges from around 0.1 wt % to 8 wt %, more typically from 1 wt % to 7 wt %, based on the weight of the amlodipine, besylate and water. In terms of molar ratio, the amount of amlodipine to water in the crystal is within the range of 1 to 0.3–2.2, more typically 0.8 to 2.2.

Two preferred hydrates are referred to herein as the monohydrate and the dihydrate. These forms contain, respectively, approximately one equivalent of water or approximately two equivalents of water. Generally the monohydrate contains 0.8 to 1.2 moles of water per each mole of amlodipine. Similarly, the dihydrate contains 1.8 to 2.2 moles of water for each mole of amlodipine. In terms of weight, the monohydrate form contains about 2.5 to 3.7 wt %, preferably 3.0 to 3.4 wt %, water while the dihydrate contains about 5.4 to 6.5 wt %, preferably 5.8 to 6.4 wt %, water. The monohydrate and the dihydrate have different crystalline structures from each other and from the prior art anhydrate form.

The hydrate forms can generally be dried to remove a portion or all of the bound water. The monohydrate and dihydrate forms can be dried, typically at 40° C. or less, to create corresponding, previously unknown, anhydrate forms. However, the crystal lattice remains, apparently essentially unchanged, as upon exposure to air/moisture the corresponding anhydrate forms will take up water and reform the initial hydrated form. That is, the monohydrate can be dried to become the corresponding anhydrate, which in turn tends to re-uptake water to reform the monohydrate. Similarly, the anhydrate form corresponding to the dihydrate tends to re-uptake water until the dihydrate is formed. It is surprising that the salt form should exhibit such a "memory" of its original form; i.e. the anhydrate corresponding to the monohydrate form does not continue taking up water until it forms the dihydrate but instead stops at approximately the original monohydrate ratio of amlodipine to water (about 1:1). Thus the monohydrate and dihydrate crystals are isomorphic to corresponding anhydrates in that destroying the bond to the water molecule apparently does not destroy or disrupt the crystal lattice. Single crystal X-ray studies reveal that the crystal structure of these isomorphic hydrates contain "channels" in which the water is bound. The water molecule can be liberated from the crystal lattice with minimal changes to the amlodipine or besylate bonds/positions.

A preferred substance of the present invention is a crystalline pharmaceutical substance comprising a repeating lattice structure that is formed of the following molecules: (a) amlodipine, an ion thereof, or both; (b) benzene sulfonic acid, an ion thereof, or both; and (c) water. The amlodipine and/or ion thereof is generally contained in a molar ratio of 1:1 with the benzene sulfonic acid and/or ion thereof. The water, (c), is generally contained in an amount of 0.8 to 2.2 moles per 1 mole of amlodipine and/or ion thereof, (a), more preferably approximately 1:1 or 2:1. The amlodipine ion is normally a cation while the benzene sulfonic acid is normally an anion. The substance can contain other compounds such as impurities therein. However, the substance is of sufficient quality to be useful as a pharmaceutical and is generally at least 98% pure, more preferably at least 99% pure. And while the lattice can contain additional compounds beyond compounds (a), (b), and (c), such compounds are generally defects in the lattice and do not occur with sufficient frequency and regularity to be considered as part of a repeating lattice structure. The presence of a repeating lattice structure can be detected, inter alia, by the existence of diffraction peaks in X-ray diffraction analysis. The substance generally has a substantially white color and is preferably in the form of particles having an average particle size of 100 microns or less, more preferably 50 microns or less, still more preferably 10 microns or less. In some embodiments, all particles in the population satisfy these size limits. The substance can be formed, inter alia, by crystallizing an aqueous solution containing amlodipine and benzene sulfonic acid, including an aqueous solution of amlodipine besylate, as described hereinafter. Milling or micronizing, optionally with sieving, can be performed to obtain the desired particle size(s), if needed. The pharmaceutical substance can be used in a pharmaceutical composition as the active ingredient in the same manner as the amlodipine besylate compounds of the present invention and as is hereinafter further described.

Novel amlodipine besylate anhydrate forms represent another aspect of the present invention. Any crystalline amlodipine besylate that is substantially free of bound water is included within the anhydrates of the present invention, except for the known prior art amlodipine besylate anhydrate form having a first melting point in the range of 201° C. to 205° C. This melting point range refers to the first melting point of the anhydrate substance under DSC analysis. Thus, the anhydrate corresponding to the monohydrate as described above exhibits a melting peak at 102° C. followed by a crystallization and a subsequent melting in the 201° C. to 205° C. range. Such a material is within the scope of the present anhydrates as the first melting point was not in the 201° C. to 205° C. range. The anhydrates corresponding to the monohydrate and the dihydrate represent preferred anhydrates of the present invention. The anhydrate "corresponds" to the monohydrate if the anhydrate crystal structure is such that when exposed to moisture it would take up water to form the monohydrate. Likewise, the anhydrate form "corresponds" to the dihydrate when it takes up water to form the dihydrate form. In general, the hydrates are relatively stable while the anhydrates tend to be hygroscopic.

One embodiment of the present invention relates to a composition that contains a mixture of amlodipine salt forms, that is, at least one amlodipine besylate anhydrate and at least one amlodipine besylate hydrate. The hydrate can be any of the amlodipine besylate hydrate forms mentioned above and is preferably the monohydrate and/or dihydrate form. The anhydrate form can be any anhydrate of amlodipine besylate including the known prior art form; i.e. including the anhydrate form that exhibits a first melting point in the range of 201° C. to 205° C. The amount of anhydrate is within the range of 0.01% to 99.99% based on the combined weight of said anhydrate and hydrate salts. In some embodiments, the anhydrate form(s) is the predominant form, accounting for 90% to 99.99%, typically 90% to 99.9%. In other embodiments, the hydrate form(s) is the predominant form and only a small portion of an anhydrate form(s) is present, such as 0.01% to 20%, more typically 0.1% to 10%.

The crystalline amlodipine salt forms can be made by any suitable crystallization technique optionally with a subsequent conversion step. Generally, a solution of amlodipine besylate is formed, either directly or through a salt forming chemical reaction. Crystalline forms can be precipitated from the solution, while amorphous forms can be formed, e.g., by freeze drying the solution. The solvent used is not particularly limited and includes an organic solvent, an aqueous solvent and mixed solvents. Preferred solvents include water, alcohols, industrial methylated spirits, and mixtures thereof.

However, a specific aspect of the present invention is the formation of various amlodipine salt forms from an aqueous solvent medium. All of the amlodipine besylate hydrate and anhydrate forms can be made from an aqueous medium, either directly or with an optional conversion. An "aqueous medium" as used herein means that a water based solvent system is used. Organic solvents such as alcohols are included only in minor amounts up to 10 wt %, preferably up to 1 wt %, and more preferably are totally absent. The hydrate forms and the anhydrate forms can be prepared by forming a solid salt form from an aqueous medium. The medium can contain any salt form of amlodipine besylate dissolved therein, or amlodipine free base can be reacted with benzenesulfonic acid in the aqueous medium to form in situ the dissolved amlodipine besylate, followed by either spontaneous or forced/induced precipitation of the solid salt form. The salt can be further treated if desired, typically by heating, to obtain a different form. Surprisingly, the known prior art amlodipine besylate anhydrate form can be precipitated from an aqueous medium.

In general, higher crystallization temperatures and higher concentrations favor the formation of anhydrate forms while lower crystallization temperatures and lower concentrations favor the formation of a hydrate form in aqueous media-based precipitations. Typically the temperature for forming an anhydrate form, especially the known prior art anhydrate form, is greater than 50° C., more typically greater than 60° C., and the concentration corresponds to at least 80% saturation. Once the heated solution is formed, crystallization is normally spontaneous on cooling, but can also be induced by known techniques such as seeding, removing solvent via heating or pressure drop, etc. The hydrates can be formed at lower crystallization temperatures, generally below 45° C. such as 20° C. to 35° C., and with optionally less concentrated solutions, given the lower temperatures.

While it is a preferred aspect of the present invention to use an aqueous medium, which has advantages of in terms of, inter alia, ecology and recovery concerns, it is noted that such is not required for forming the salt forms of the present invention. A mixture of organic solvents and water can be used, including a major amount of organic solvent, such as 90% ethanol with 10% water. Also, crystallization can be induced by adding water as a contra solvent to an organic solution of amlodipine besylate. All of these techniques are useful in forming the compounds of the present invention.

Any purification technique may be further used in the manufacturing process to improve chemical purity or solid state properties, if desired or needed. For instance, a filtration of the solution with an adsorbent, e.g. activated charcoal, or slurrying the formed solid with an organic liquid, can improve the color of the product. In this regard, the final amlodipine besylate compound, or mixture of amlodipine besylate compounds, should preferably exhibit a substantially white color, i.e. white or nearly white. Rather surprisingly, slurrying the crude amlodipine besylate hydrate in an organic liquid, followed by isolation of the solid, e.g. by filtration, is more efficient for removing coloring impurities, if present, e.g., from the route of synthesis, than a conventional treatment of the solution with an adsorbent. Accordingly, while an adsorbent, such as charcoal, may be present in the slurry, it is preferably omitted; i.e., not present therein. The slurrying process can moreover proceed at ambient temperature, thus decreasing the potential for forming degradation products. The "crude" amlodipine besylate hydrate used in the process includes amlodipine besylate hydrate isolated or obtained directly from its synthetic reaction media as well as any amlodipine besylate monohydrate that has a color, e.g. is not substantially white. A suitable organic liquid includes $C_1$–$C_6$ aliphatic ketones, aliphatic esters or aliphatic hydrocarbons or mixtures thereof, but is not limited thereto. Preferably the organic liquid is methyl isobutyl ketone or an ethyl acetate/hexane mixture.

It should be noted that the amlodipine besylate hydrates, particularly the monohydrate, are surprisingly equivalent to the known prior art amlodipine besylate anhydrate form as far as stability in solid state and in solution are concerned. Moreover, particularly the light sensitivity of the monohydrate is slightly less in comparison to the known anhydrate.

As mentioned previously, the desired amlodipine besylate may be formed via an optional conversion step. The hydrate and anhydrate forms are often convertible from one form to the other, normally by the use of heating and/or exposure to moisture. The hydrate form can be converted into a different hydrate form or into an anhydrate form by heating. In this regard, the monohydrate form is generally more stable than the dihydrate form. Sufficient heating, generally greater than 65° C., and for a sufficient time (i.e. annealing), can cause a conversion of the hydrate form to the known prior art anhydrate form. While such a heat treatment may be convenient for production purposes, the relatively high thermodynamic barrier means that the amlodipine besylate hydrates will not convert into the known amlodipine besylate anhydrate under the conditions encountered by a pharmaceutical in the ordinary course of manufacture, storage and use. Nonetheless, when drying any of the novel forms of the present invention, especially on a commercial scale, heating at temperatures of not more than 60° C., preferably 20° C. to 50° C. are typically used, unless a conversion to the known prior art anhydrate is not of concern or is desired. These same lower temperatures are normally used to convert a hydrate to a corresponding anhydrate of the present invention such as by vacuum drying. By the use of conversion, the amount of bound water can be controlled to within the disclosed range.

Another form that can be made from an aqueous medium is an amorphous amlodipine besylate salt. Such forms are conveniently prepared by freeze drying an aqueous solution of amlodipine besylate. The amorphous form is especially useful in making various encapsulated dosage forms including conventional capsules (gelatin capsules filled with the active and excipients) as well as microcapsules, but is not limited thereto.

The amlodipine besylate forms of the present invention are useful as intermediates and/or as pharmaceutically active agents, particularly as calcium channel blockers. Thus, the amlodipine besylate forms, alone or in combination, can be used to treat any cardiac condition that would be benefited by administration of a calcium channel blocker. In particular, the amlodipine besylate forms can be used to treat or prevent hypertension, congestive heart failure, or angina pectoris by administering an effective amount to a patient in need thereof. The specific form of angina is not particularly limited and specifically includes chronic stable angina pectoris and vasospastic angina (Prinzmetal's angina). The compound can be administered by any suitable route including orally or parenterally. The "patients" intended to be treated include human and non-human animals especially humans and non-human mammals.

The compound is usually administered as part of a pharmaceutical composition. Accordingly, a further aspect of the invention is a pharmaceutical composition that comprises amlodipine besylate hydrate, a mixture of amlodipine besylate forms, or an amlodipine besylate anhydrate not having a first melting point within the range of 201° C. to 205° C., and a pharmaceutically acceptable excipient. Preferably the pharmaceutical composition contains an effective amount of the amlodipine besylate hydrate or an effective amount of a mixture of amlodipine besylate salt forms, especially a mixture that contains an amlodipine besylate hydrate, or an effective amount of an amlodipine besylate anhydrate not having a first melting point within the range of 201° C. to 205° C., for treating or preventing hypertension, congestive heart failure or angina. The mixture of amlodipine besylate forms can have the ratios and components as described above, and is preferably a mixture that contains at least one amlodipine besylate hydrate, especially the monohydrate, and at least one amlodipine besylate anhydrate. Preferred compound for making pharmaceutical formulations is amlodipine besylate monohydrate.

Excipients include any inert or non-active material used in making a pharmaceutical dosage form. For example, tablet excipients include, but are not limited to, calcium phosphate, cellulose(s), starch or lactose. Capsules such as those made of gelatin, may contain or carry amlodipine besylate alone or in admixture with other excipients. Liquid dosage forms are also included such as oral liquids in the form of liquors or suspensions, as well as injectable solutions. The pharmaceutical composition may be formulated for transdermal administration in the form of a patch. All of the above described pharmaceutical compositions may optionally contain one or more of each of the following excipients: carriers, diluents, colorants, flavoring agents, lubricants, solubilizing agents, disintegrants, binders and preservatives.

The pharmaceutical composition is normally provided in a unit dose. A unit dose is typically administered once or twice daily, more typically once daily. In the case of a transdermal patch, the unit dose (one patch) is generally applied at least once a month, more commonly at least once a bi-week, and typically once a week. An effective amount in a unit dose for treating or preventing hypertension, congestive heart failure, or angina is generally within the range of 1 to 100 mg, typically 1 to 50 mg, more typically 1 to 20 mg. In solid oral dosage forms (tablets, capsules, etc.), the pharmaceutical composition typically contains about 1, 2.5, 5.0, or 10 mg of the amlodipine besylate. For simplicity, all amounts refer to the corresponding amount of amlodipine free base provided to the composition. Specific examples of pharmaceutical compositions include those described in EP 244944.

The pharmaceutical composition may be combined with additional pharmaceutically active agents. For example, compositions of the invention may be also used in medical applications in combination with other antihypertensive and/or antianginal agents, for instance with ACE-inhibitors such as benazepril, with beta-blocker(s) or with nitrates. The combination may be realized in a form of single combination preparation, e.g. a capsule containing amlodipine besylate and benazepril hydrochloride, or by separate administration of drugs containing the above agents. Similarly, amlodipine besylate may also be combined with HMG-CoA reductase inhibitors such as lovastatin, simvastatin, atorvastatin as well as other statins.

All of the pharmaceutical compositions described above can be made by known methods and techniques. For example, the tablets can be made by dry granulation/direct compression or by a classical wet granulation method. Typically, tablets are made by blending, filling and compressing into tablets. The blending step may comprise a wet granulation or dry granulation. Similarly, capsules can be made by blending the ingredients and filling the capsule.

For use in pharmaceutical compositions, preferably for making solid pharmaceutical dosage forms, the amlodipine besylate hydrates and the anhydrate forms of the present invention are advantageously manufactured within a specific particle size. The preferred product for making solid pharmaceutical compositions has the average particle size of 100 microns or less, preferably 50 microns or less and more preferably 10 microns or less. Advantageously, the whole population of particles within the product is 100 microns or less, more preferably 50 microns or less and still more preferably 10 microns or less. Such product may be obtained directly by the method of manufacture/formation of the amlodipine besylate compound, e.g. by proper selection of the precipitation conditions and techniques, or alternatively, by any conventional way of milling or micronization optionally with sieving.

The invention will be further illustrated by the following examples, but should not be taken as being limited thereto.

EXAMPLE 1

Dihydrates

1(a). 2 g of amlodipine besylate salt was dissolved in 50 ml of water at reflux. The solution was allowed to cool to room temperature. After standing for 1 night at room temperature, the solid was filtered off and washed with 2 ml of water. The solid was dried in a vacuum oven at about 25° C. for 2 days. The material gives an IR spectrum as shown in FIG. 1.

Figure 2:
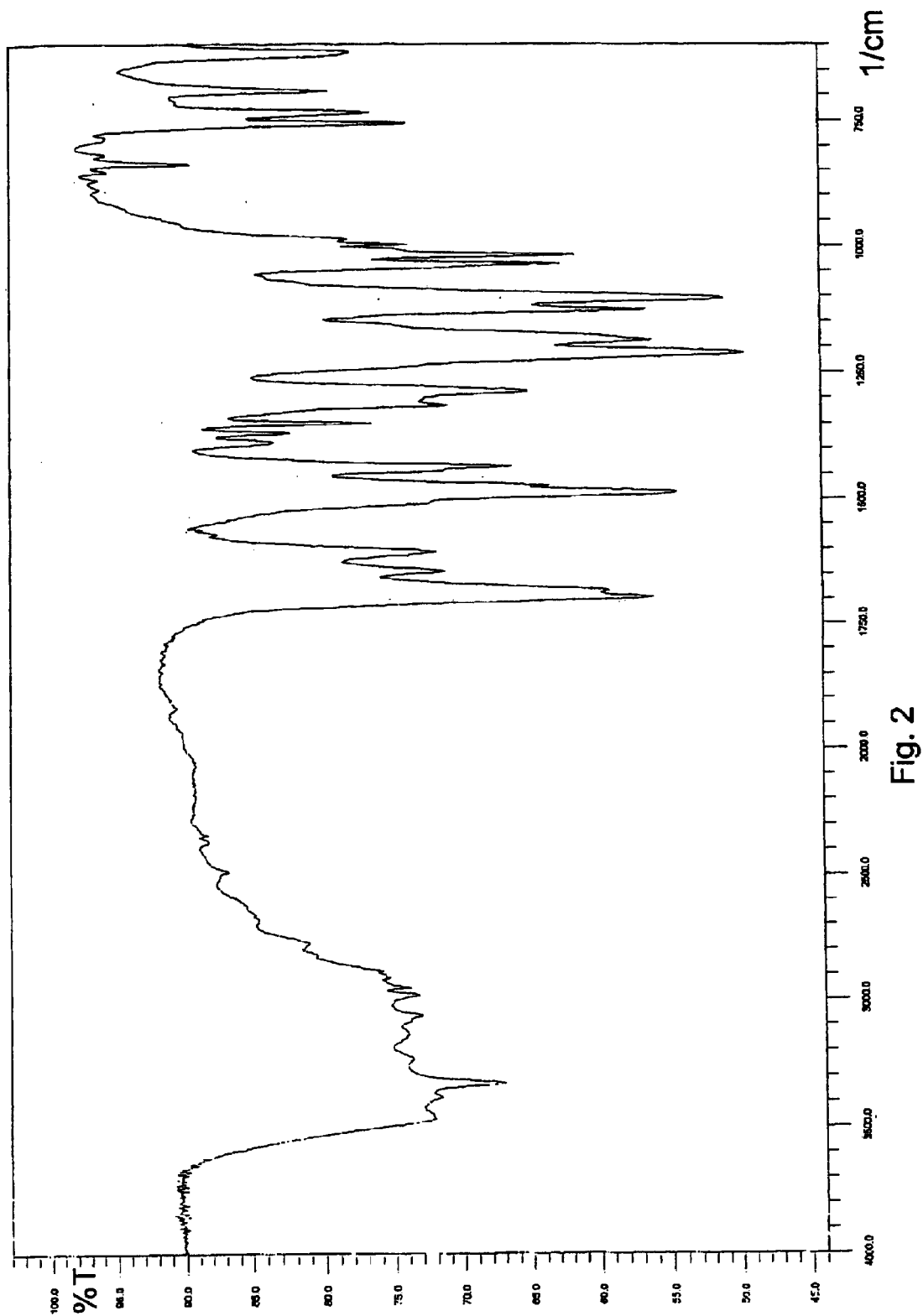
FIG. 2 shows an IR spectrum for the anhydrate salt of example 1(b).

1(b). 735.1 mg of the product of example 1(a) was dried in a vacuum oven at 40° C. for 65 hours. The weight loss was 0.043 g or 5.85%, which corresponds to 1.9 moles of water per mole of amlodipine. This anhydrate of the corresponding dihydrate form gives an IR as shown in FIG. 2.

1(c). A sample of the anhydrate formed in example 1(b) was exposed to air and the weight gain recorded as follows:

| | |
|---|---|
| Weight at start: | 103.1 mg |
| Weight after 30 min | 105.7 mg |
| Weight after 1 hour | 107.3 mg |
| Weight after 3.5 hour | 109.3 mg |
| Weight after 21 hour | 109.3 mg |

Figure 3:
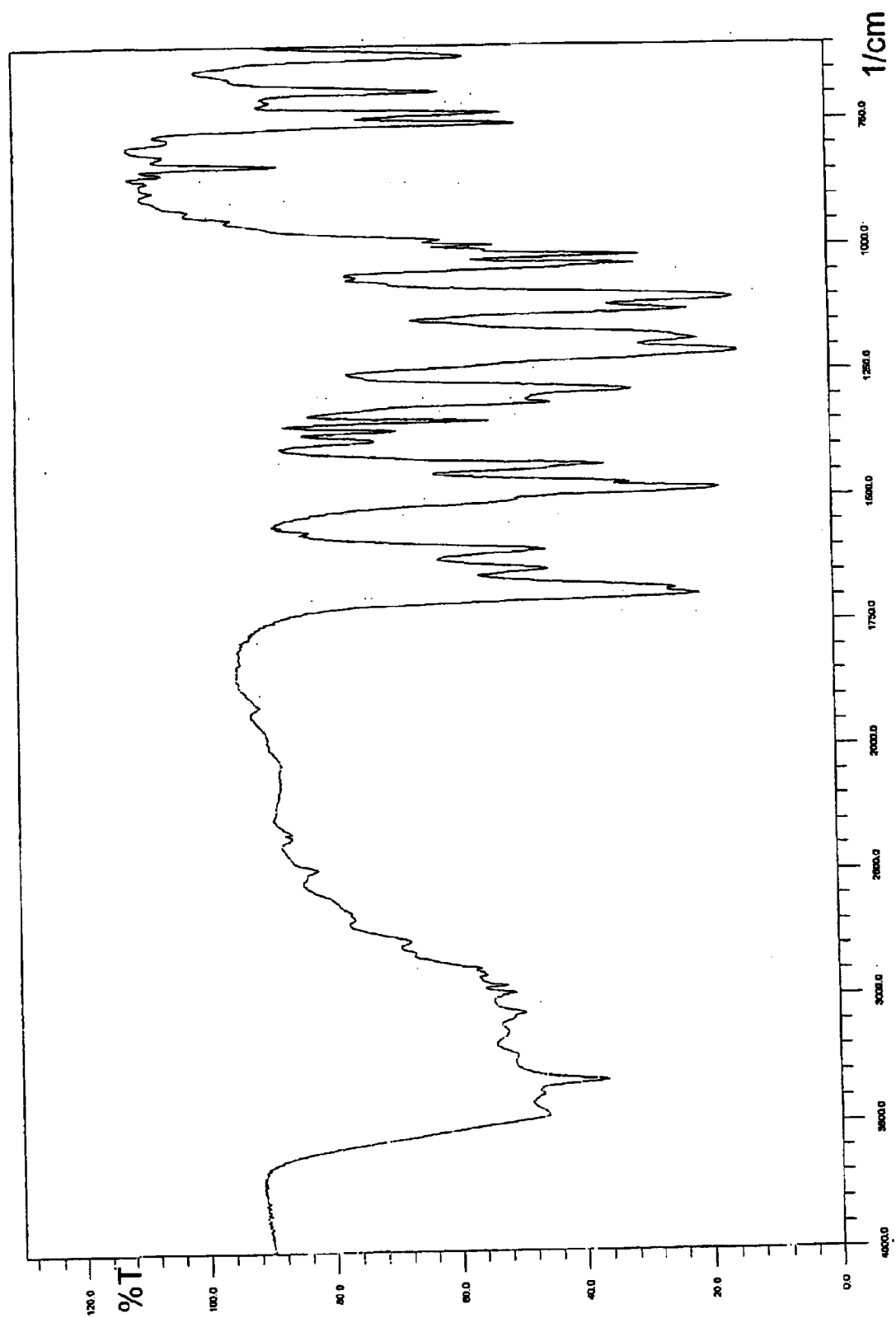
FIG. 3 shows an IR spectrum for the dihydrate salt of example 1(c).

Total weight gain of 6.2 mg or 6.0%, which corresponds to two moles of water taken up for one mole of amlodipine. This re-formed dihydrate has an IR spectrum as shown in FIG. 3.

Figure 4:
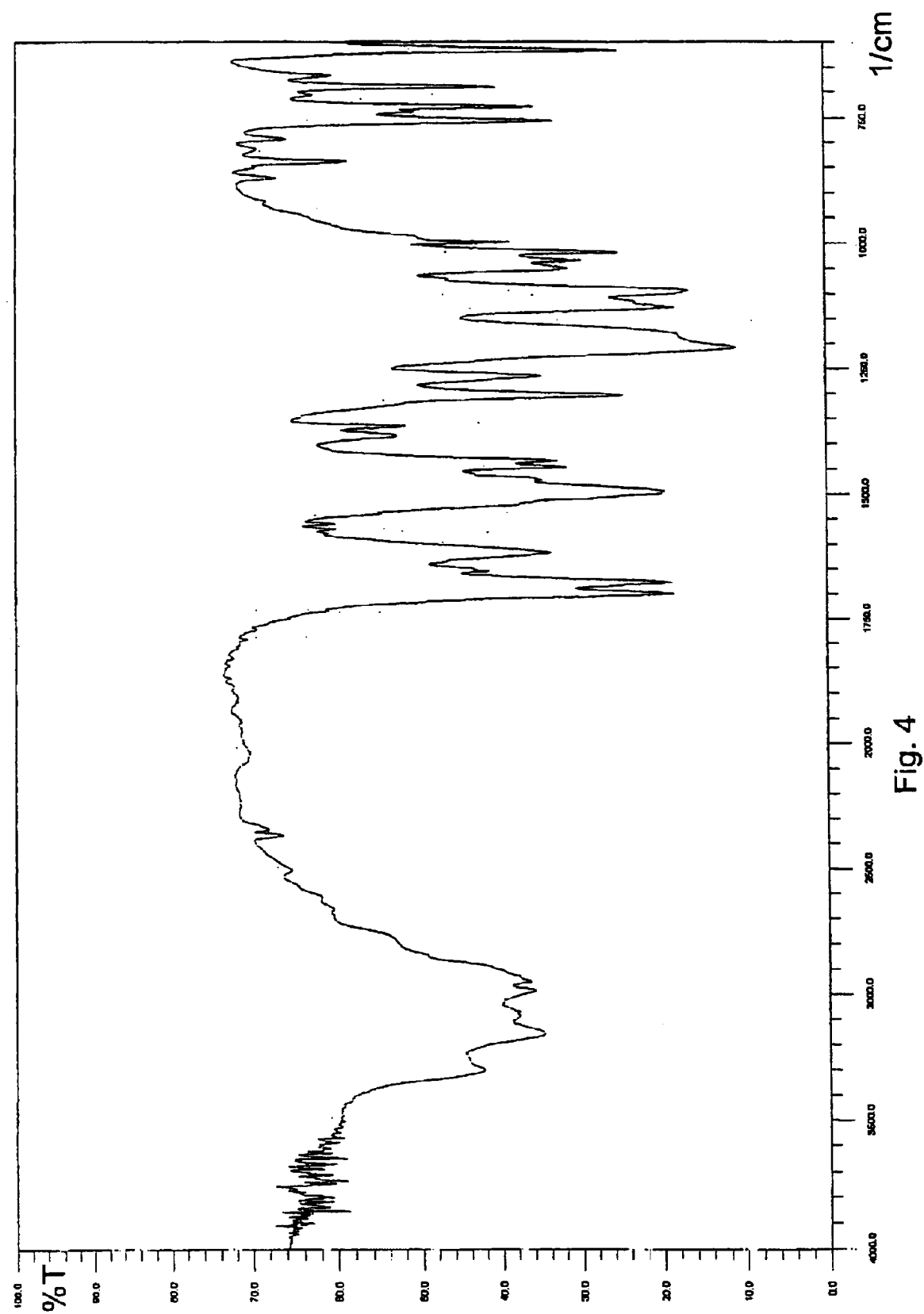
FIGS. 4 and 5 show the IR spectra for the annealed products of example 1 (d), which correspond to the known amlodipine besylate anhydrate.
Figure 5:
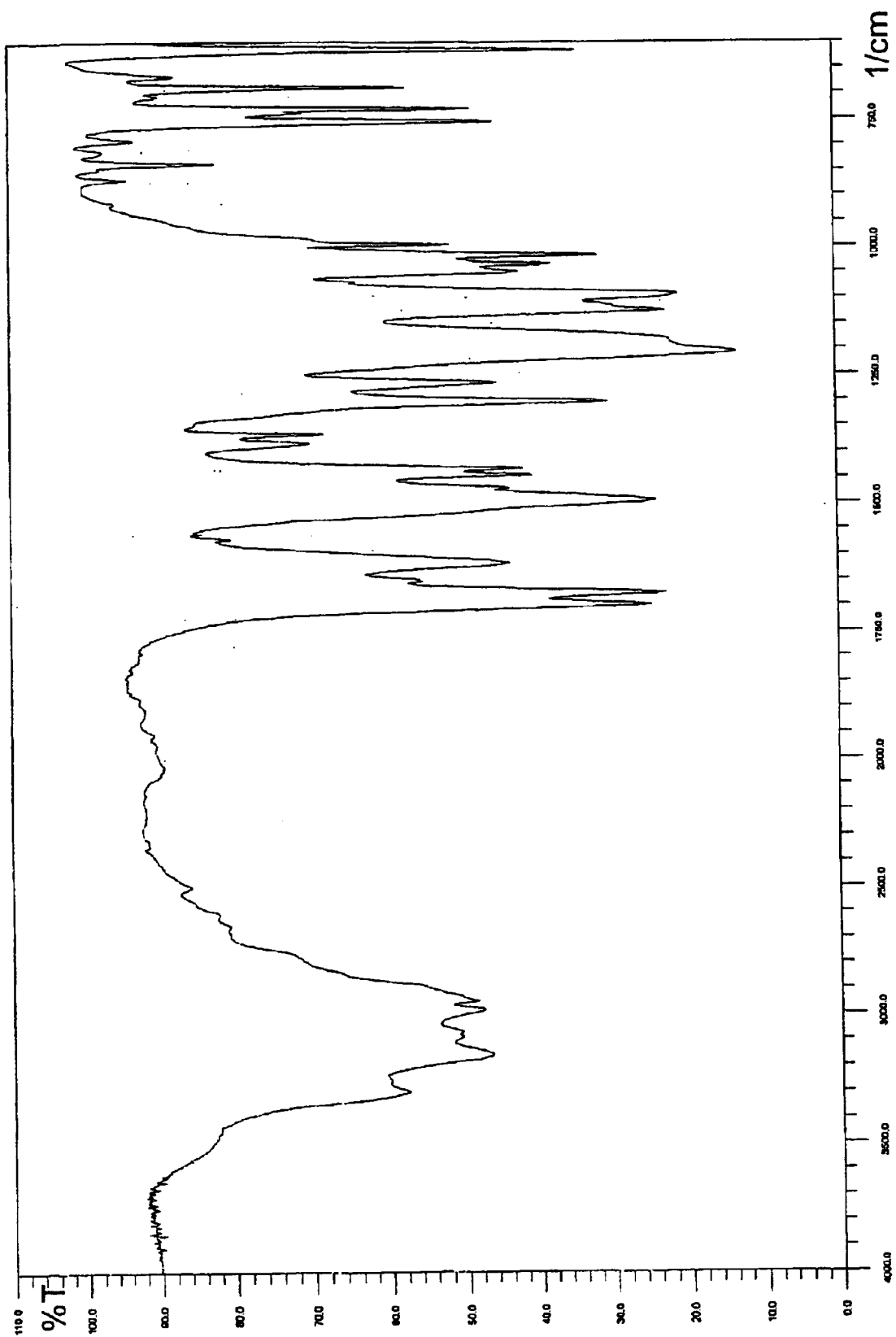

1(d). A sample from example 1(a) was annealed for 10 minutes at 90° C. while another sample of the same product was annealed for 30 minutes at 145° C. In both cases the dihydrate was converted to the known anhydrate form as shown by IR. The IR for the sample annealed for 10 minutes is as shown in FIG. 4 and the IR for the sample annealed for 30 minutes is as shown in FIG. 5.

1(e) 149.12 mg amlodipine besylate anhydrate was suspended in 3 ml water and was shaken at 37° C. at 60 RPM for 48 hours. The suspension was allowed to cool to room temperature and the solid was isolated by filtration and dried under vacuum for three hours. This leads to amlodipine besylate dihydrate. The material gives an IR spectrum similar to FIG. 1.

EXAMPLE 2

Monohydrates

Figure 6:
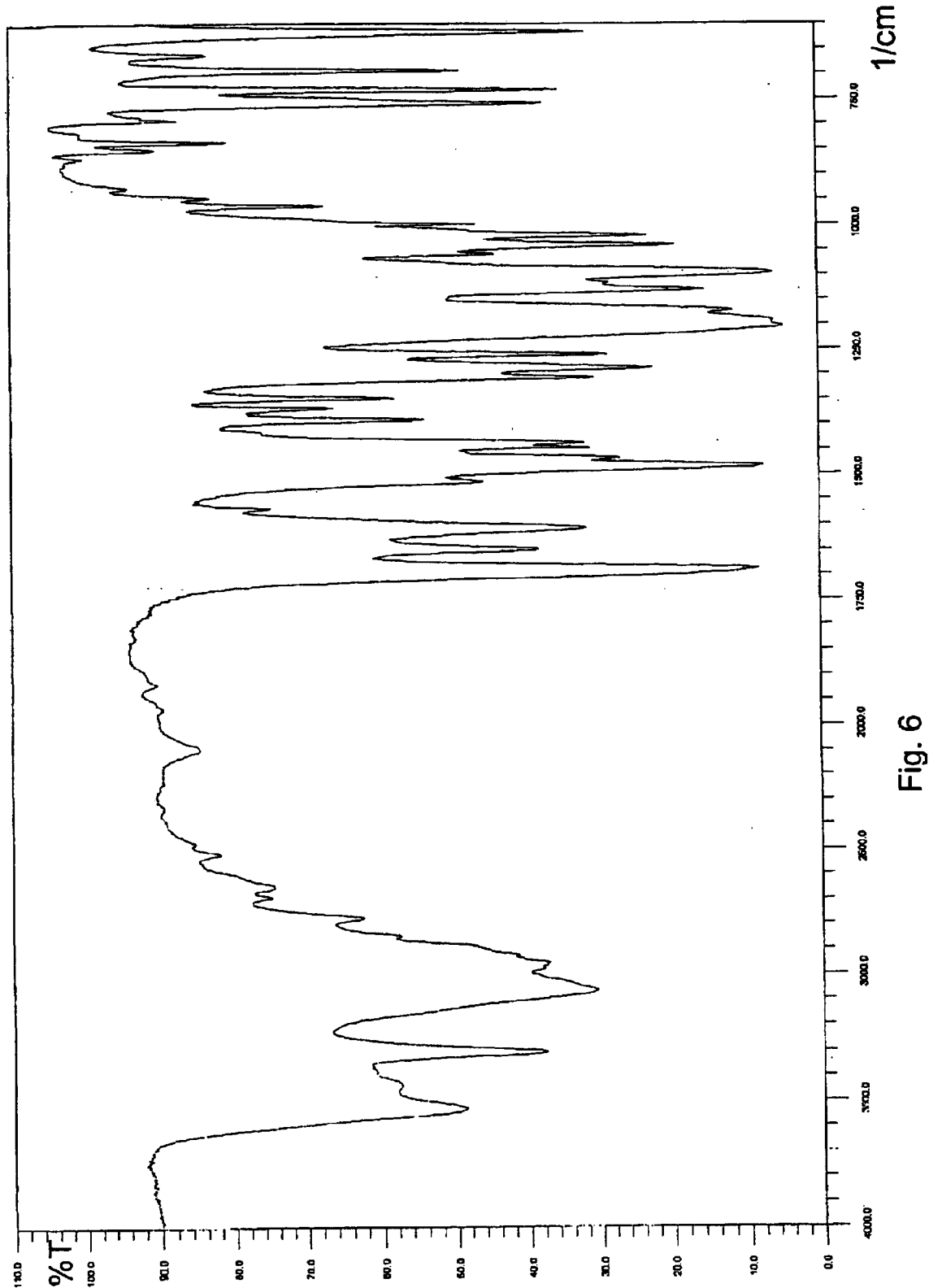
FIG. 6 shows an IR spectrum for the monohydrate salt of example 2(a).

2(a). 4 g of amlodipine besylate salt was added to 200 ml of water, which was heated to 90° C. A solution was obtained, which was allowed to cool to room temperature. At 60° C., 2 ml of the clear solution was taken out and put in a test-tube. The test-tube was placed in a water bath at 20° C. and amlodipine besylate readily crystallized. 1 drop of the suspension from the test-tube was added to the remaining amlodipine besylate solution (at 58° C.). Crystallization started at 55° C. After the suspension was cooled down to 20° C., the solid was isolated by filtration and washed with 2×2 ml of water and dried in a vacuum oven at 40° C. for 16 hours to form a substantial or complete anhydrate of the monohydrate crystal. The yield was 3.18 g of an amlodipine besylate having a melting point on DSC at 92.1–103.9° C.; solidifies at 119.1–130.0° C.; melting and degradation at 196.0–202.4° C. (rate 5° C./min). The material has an IR as shown in FIG. 6.

2(b). A sample of the dried amlodipine besylate from example 2(a) was exposed to air and the weight gain recorded as follows:

| | |
|---|---|
| Weight at start: | 318.6 mg |
| Weight after 30 min | 320.3 mg |
| Weight after 1 hour | 323.9 mg |
| Weight after 3.5 hour | 328.2 mg |
| Weight after 21 hour | 328.2 mg |

Figure 7:
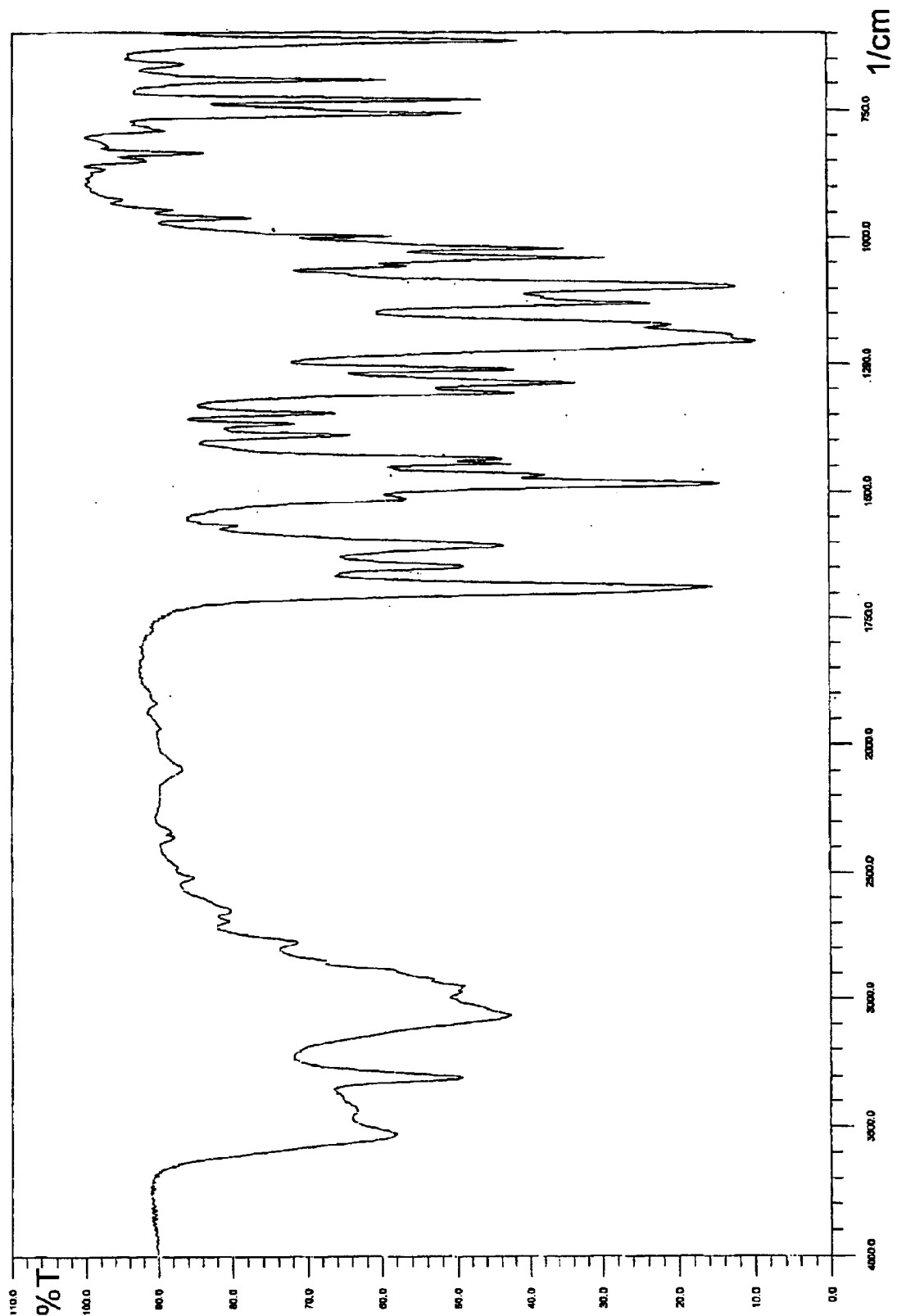
FIG. 7 shows an IR spectrum for the monohydrate salt of example 2(b).

Total weight gain was 6.2 mg or 3.0 wt %, which corresponds to one mole of water being taken up for one mole of amlodipine. Thus, the material is a monohydrate and has an IR as shown in FIG. 7.

Figure 8:
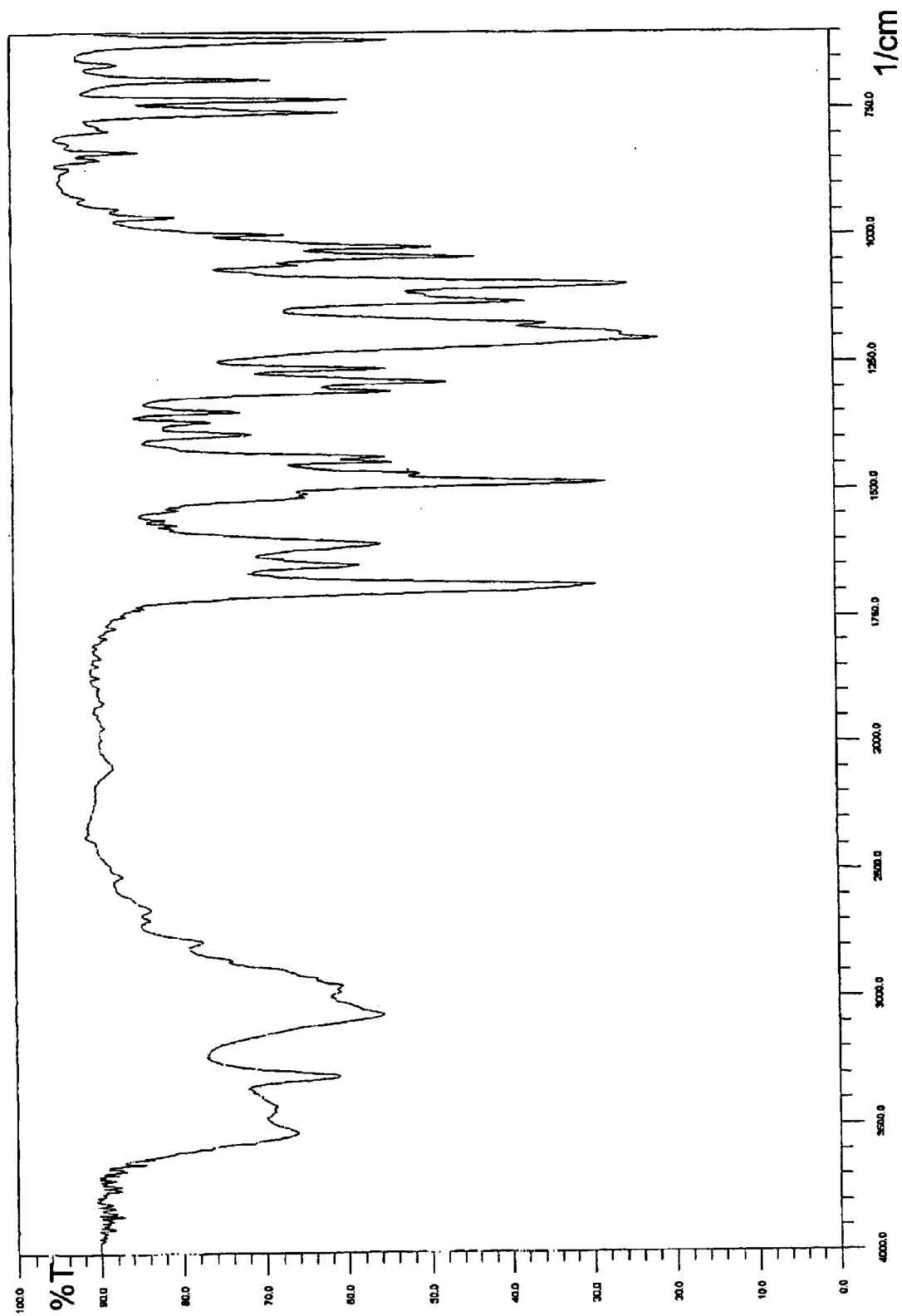
FIG. 8 shows an IR spectrum for the monohydrate salt of example 2(c).

2(c). 1.9 g of benzenesulfonic acid.$XH_2O$ was dissolved in water. The solution was heated to 40° C. At 40° C., while stirring, 4.0 g of amlodipine free base was added portion-wise in 10 minutes. The resulting suspension was stirred at 40° C. for 1 hour and allowed to cool to room temperature (without stirring) and set aside at room temperature for 16 hours. The solid was filtered off and washed with 5.0 ml of water. The solid was dried in a vacuum oven at 40° C. for 16 hours. The yield was 5.4 g of an amlodipine besylate monohydrate salt having an IR as shown in FIG. 8.

EXAMPLE 3

Powder X-Ray Diffraction

Figure 9:
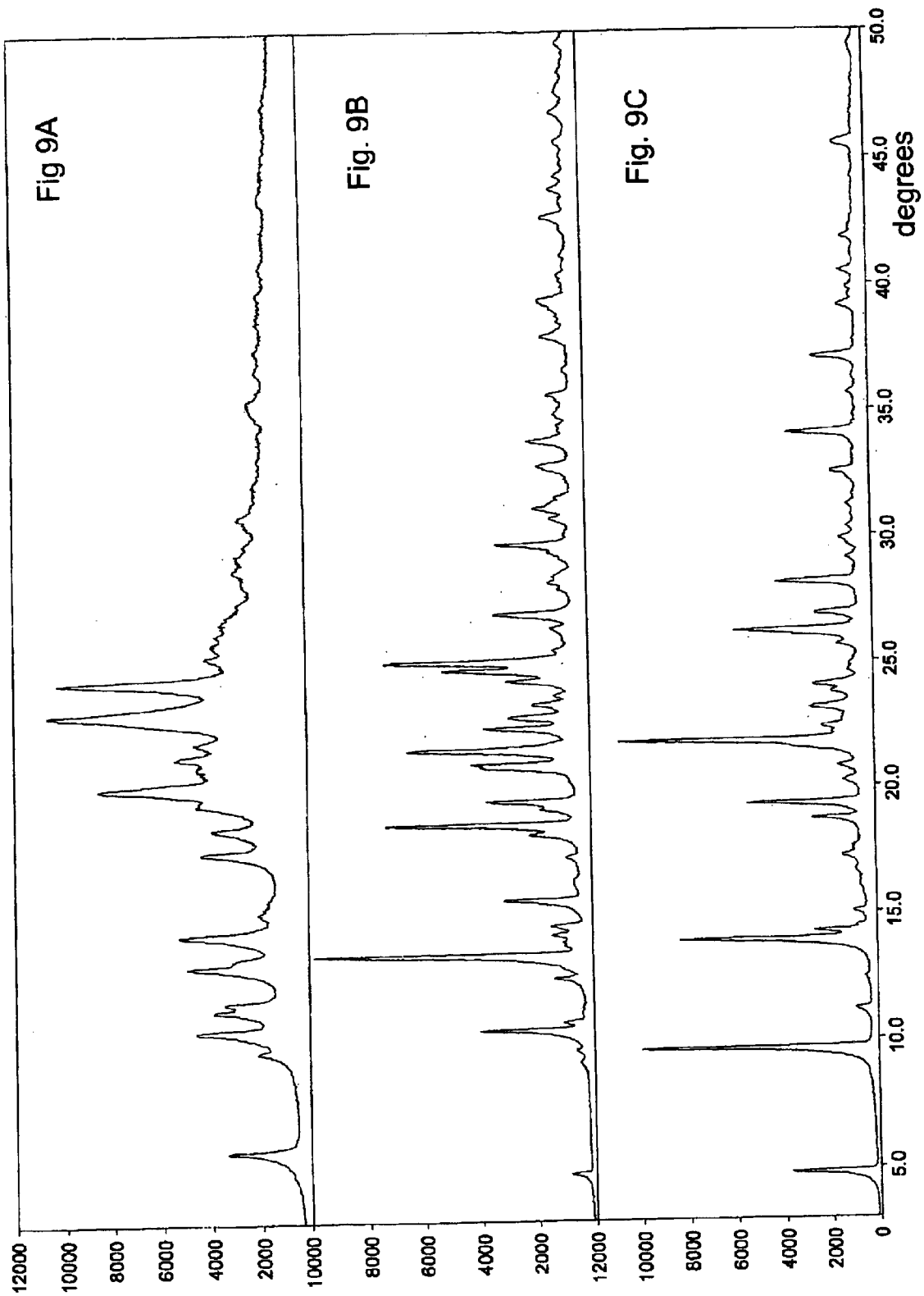
FIGS. 9A–9C show the powder X-ray diffraction pattern for the known amlodipine besylate anhydrate, the dihydrate of example 1 (a) and the monohydrate of example 2(a), respectively.

Sample of amlodipine dihydrate from example 1(a) and amlodipine monohydrate from example 2(a) (having been sufficiently exposed to air) were subjected to x-ray powder diffraction (powder-XRD). For comparison, an amlodipine besylate anhydrate corresponding to the known form was also subjected to powder-XRD. The results are shown in FIGS. 9A–9C wherein 9A is the known anhydrate form, 9B is the dihydrate form and 9C is the monohydrate form. Both hydrate forms have a peak around 33–34 degrees and a peak at about 37 degrees while the known anhydrate has neither. Indeed, the dihydrate and monohydrate crystalline forms of the present invention can be distinguished from each other and the known anhydrate form based on these, and other, peaks in the powder XRD. A preferred embodiment of the present invention is a crystalline amlodipine besylate having an X-ray diffraction peak in at least one of the 33–34 degree range or about 37 degrees. Such a crystal may contain bound water or not. In some embodiments, such a crystal preferably may add or lose bound water without significantly changing the crystal lattice and most preferably may add or lose bound water reversibly the same amount; i.e., the monohydrate based crystal takes up about one equivalent of water into the lattice but not 2 equivalents.

EXAMPLE 4

Figure 10:
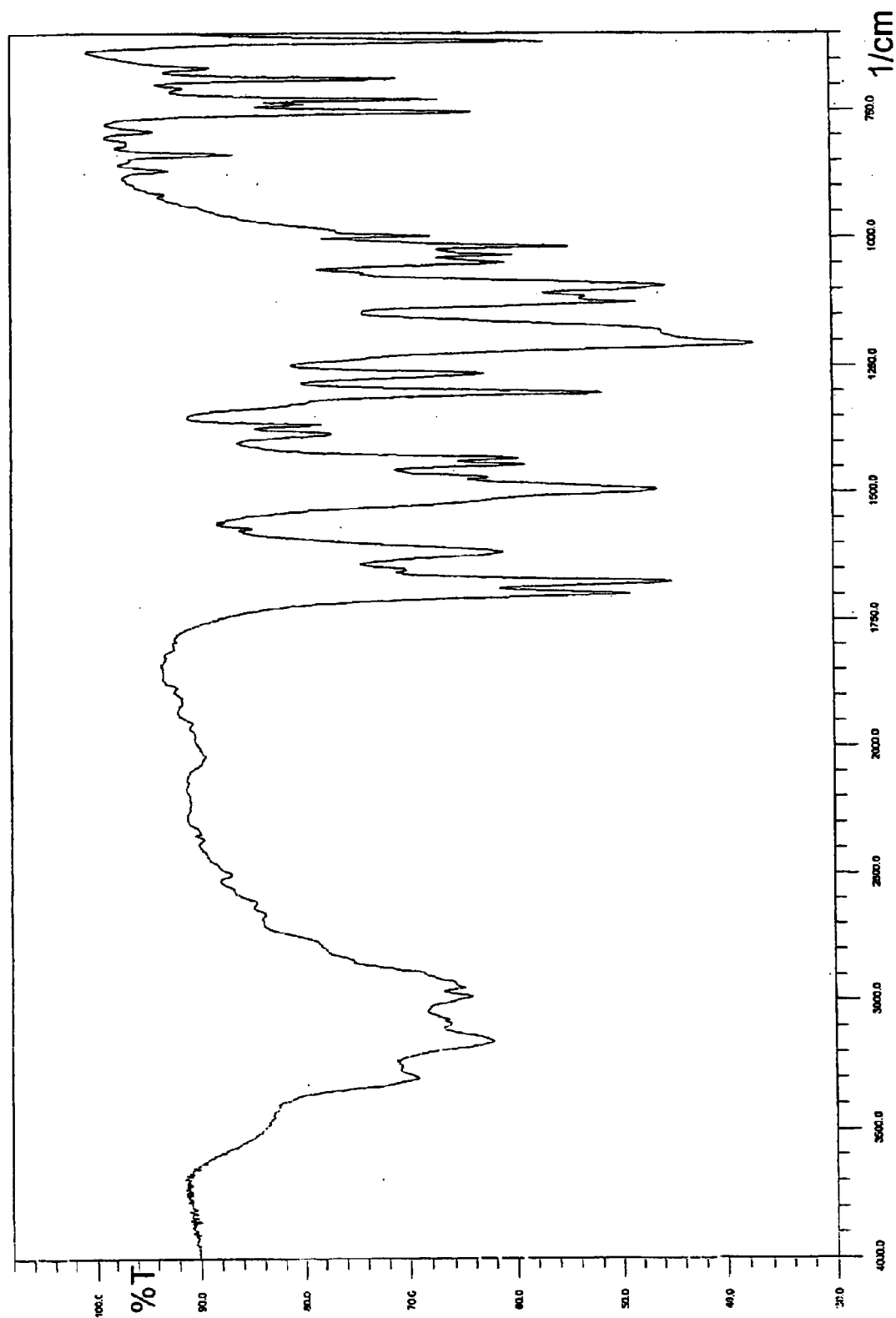
FIG. 10 shows the IR spectrum for the anhydrate salt produced in example 4.

150 ml of water was heated to reflux whereupon 35 g of amlodipine besylate was added and 15 ml of water was used to wash the powder funnel. A clear solution was obtained. The solution was set aside at 60° C. After 4 hours standing at 60° C., the solution was inoculated (seeded) with dihydrate salt from example 1(a) and set again at 60° C. After 1 night at 60° C. the formed solid was filtered off and washed with 2×20 ml of water and dried in a vacuum oven at 40° C. The yield was 30.5 g of the known amlodipine besylate anhydrate having an IR as shown in FIG. 10.

EXAMPLE 5

Figure 11:
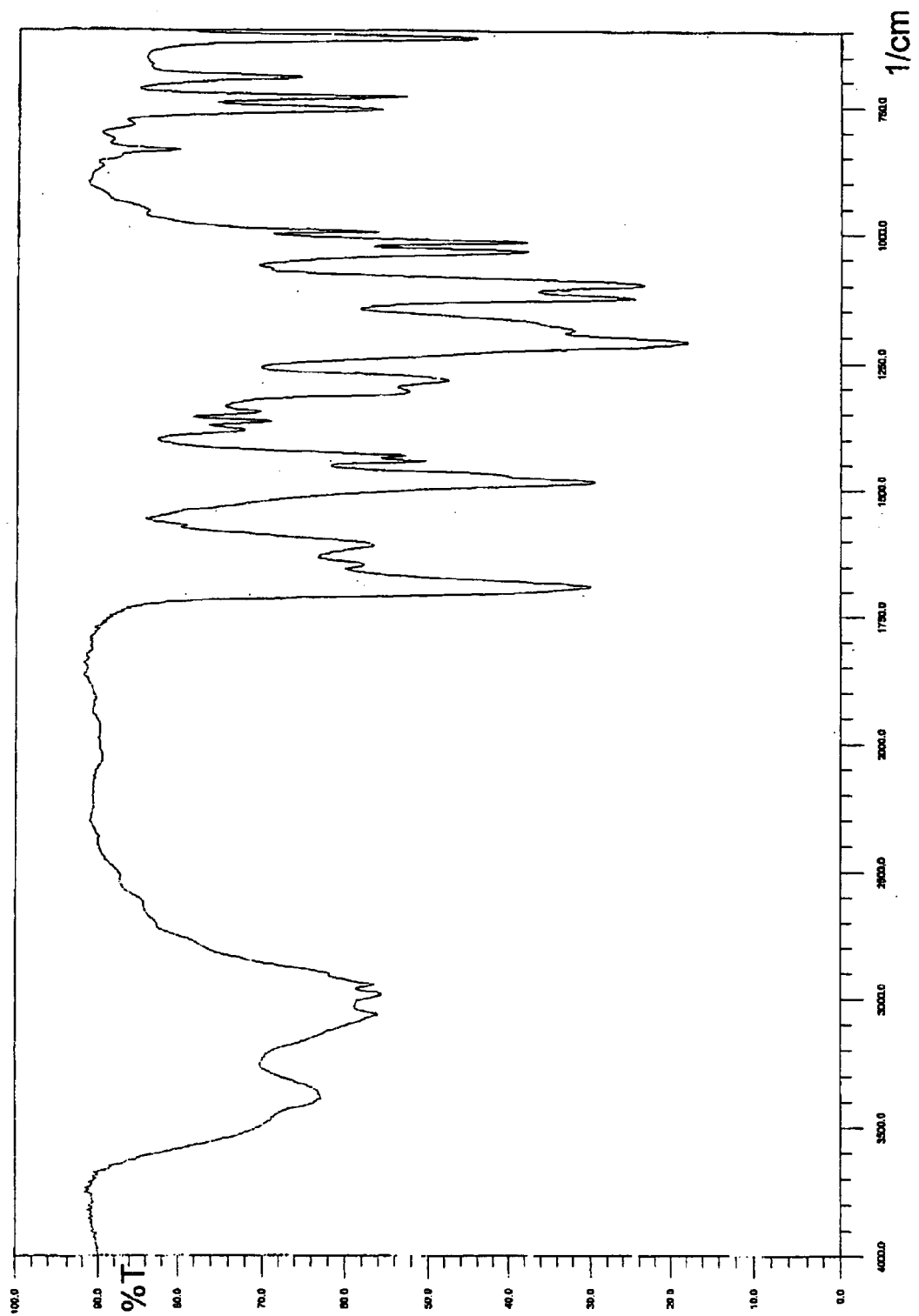
FIG. 11 shows the IR spectrum for the amorphous amlodipine besylate salt produced in example 5.

200 mg of amlodipine besylate was dissolved in water at reflux. The hot solution was cooled in a cardice-acetone bath. The frozen solution was freeze-dried resulting in an amorphous amlodipine besylate salt form having an IR as shown in FIG. 11.

EXAMPLE 6

Crystallization of Amlodipine Besylate Hydrates from Ethanol/Water

6(a) 8.57 g of amlodipine besylate was added to 25 ml of ethanol/water (50/15 v/v) in a 100 ml round-bottomed flask. The flask was heated on a water-bath at 40° C. until the solid was dissolved. The solution was filtered through a 0.45 $\mu$M filter and the filtrate was set in a water-bath, which was heated to 40° C. every three hours for a period of one hour. The solution was allowed to evaporate partly during this heating and cooling. After 1 night, a small crystal was formed. The flask was removed from the water-bath and was allowed to cool to room temperature. After three days, the flask was filled with big, square flat crystals. The crystals were analyzed to confirm the dihydrate form and were used to measure single crystal X-ray diffraction pattern.

6(b) 1.5 g amlodipine besylate monohydrate was suspended in 4.0 ml ethanol and 6.0 ml water. The mixture was heated to 70° C. A clear solution was obtained. The solution was placed in a water-bath at 35° C. and the water-bath was allowed to slowly cool to room temperature. After 16 hours, the temperature was 25.8° C., no crystals were formed. The solution was seeded with a few crystals of the monohydrate. Crystallization started. After 2 days, a few crystals were taken out of the flask and dried on air for 1 hour. I.R. spectrum was measured. (monohydrate). The flask containing the crystals was used to measure single crystal X-ray diffraction pattern.

EXAMPLE 7

Amlodipine Besylate Monohydrate

7(a) 35 g benzenesulfonic acid was dissolved in 600 ml water and heated to 70° C. 90 g of amlodipine base was added and the resulting suspension was heated to 85° C. It became a clear solution. The solution was stirred for 30 minutes at 85° C. and allowed to cool to room temperature while stirring. At 50° C. the solution was seeded with a few crystals of amlodipine besylate monohydrate. Crystallization started very quick and very small particles were obtained. After cooling the suspension to room temperature it was stirred for 2 hours at room temperature. The solid was isolated by filtration and washed with 2×150 ml water. Dried in a vacuum oven at 40° C. Yield: 120 g very fine white powder. Water content (K. Fischer titration): 3.09% (1 equivalent). Particle size <20 $\mu$m.

7(b) 180 g amlodipine was suspended in 1000 ml water and heated to 60° C. 70 g benzenesulfonic acid was dissolved in 200 ml water and added to the suspension. The resulting mixture was heated to 85° C. and stirred for 30 minutes. It became a clear solution. The stirred solution was allowed to cool to 65° C. and was seeded with 100 mg of amlodipine besylate monohydrate. Crystallization started and the suspension was allowed to cool slowly to room temperature. After cooling to room temperature, the suspension was set aside for 16 hours. The solid was isolated by filtration and washed with 2×200 ml water. Dried in a vacuum oven at 40° C. for 2 days, the solid was exposed to air for 1 day. Yield: 249 g. Water content (K.Fischer titration): 3.09% (1 equivalent). Particle size: <250 μm.

7(c) 900 g amlodipine was suspended in 5l water and heated to 60° C. 350 g benzene sulfonic acid was dissolved in water and added to the suspension. The resulting mixture was heated to 85° C. and stirred for 30 minutes. It became a clear solution. The stirred solution was allowed to cool to 65° C. and was seeded with 200 mg amlodipine besylate monohydrate crystals. Crystallization started and the suspension was allowed to cool slowly (16 hours) to room temperature. After cooling to room temperature the solid was isolated by filtration and washed with 2×1l water. Dried in a vacuum oven at 40° C. for 2 days. The solid was then exposed to air for 1 day. Yield: 1.25 kg Amlodipine besylate monohydrate.

7(d) Improvement of Colouration

7(d)(1) 2.5 g of amlodipine besylate monohydrate from the above experiment 7(c) was dissolved in 15 ml water at 85° C. and 250 mg charcoal was added. The resulting suspension was stirred for 10 minutes at 85° C. The hot suspension was filtered over a hot filter with celite. The filtrate was allowed to cool to room temperature. The solid that was formed was isolated by filtration and dried in a vacuum oven at 40° C. for 1 night. A white crystalline powder was obtained. IR spectrum revealed the structure of amlodipine besylate monohydrate.

7(d)(2) 200 mg of amlodipine besylate monohydrate from the above experiment 7(c) was suspended in 1 ml tert-butylmethylether. The suspension was set aside for 2 hours. The solid was isolated by filtration and dried in a vacuum oven at 40° C. for 1 night. A white crystalline powder was obtained. IR spectrum revealed the structure of amlodipine besylate monohydrate.

7(d)(3) 250 mg of amlodipine besylate monohydrate from the above experiment (7C) was suspended in 2 ml of ethyl acetate/n-hexane 1:1 (v/v) mixture saturated with water. After 5 minutes, the solid was isolated by filtration and dried at air for 2 hours. A white crystalline powder was obtained. Yield: 240 mg. IR spectrum revealed the structure of amlodipine besylate monohydrate.

EXAMPLE 8

Reference

Crystals of the known prior art anhydrous amlodipine besylate suitable for X-ray diffraction studies were prepared. A single crystal was mounted in air on a glass fiber. Intensity data were collected at room temperature. An Enraf-Nonius CAD4 single-crystal diffractometer was used, CuKα radiation, ω-2θ scan mode. Unit cell dimensions were determined from the angular settings of 23 reflections. Intensity data were corrected for Lorentz and polarization effects. Semi-empirical absorption correction (ψ-scans) was applied. Basic data obtained by the measurement are listed in the Table 1.

TABLE 1

Atomic coordinates (×10$^4$) and equivalent isotropic displacement parameters (Å$^2$ × 10$^3$). $U_{eq}$ is defined as one third of the trace of the orthogonalized $U_{ij}$ tensor.

| | x | y | z | $U_{eq}$ |
|---|---|---|---|---|
| Cl(1) | −3319(3) | 2472(2) | 415(1) | 142(1) |
| S(1) | 1708(2) | 150(1) | 1833(1) | 64(1) |
| O(1) | −1783(5) | 5697(2) | 2043(1) | 58(1) |
| O(2) | −1643(11) | 5206(4) | 829(2) | 212(5) |
| O(3) | −2206(6) | 4191(3) | 530(2) | 101(2) |
| O(4) | −4931(6) | 2338(3) | 2017(2) | 97(2) |
| O(5) | −4923(6) | 2512(3) | 1302(2) | 97(2) |
| O(6) | 1396(7) | 898(3) | 1767(2) | 127(3) |
| O(7) | 727(6) | −191(4) | 2097(2) | 121(2) |
| O(8) | 2992(5) | 53(3) | 2026(1) | 101(2) |
| N(1) | −2376(6) | 4182(3) | 2054(2) | 61(2) |
| N(2) | −4215(5) | 6122(3) | 2483(2) | 62(2) |
| C(2) | −2009(6) | 4514(4) | 1670(3) | 54(2) |
| C(3) | −2319(7) | 4223(3) | 1281(2) | 55(2) |
| C(4) | −2940(7) | 3471(3) | 1257(2) | 57(2) |
| C(5) | −3548(7) | 3260(4) | 1698(2) | 51(2) |
| C(6) | −3228(8) | 3598(4) | 2071(2) | 61(2) |
| C(7) | −1182(7) | 5196(4) | 1751(3) | 70(2) |
| C(8) | −2784(7) | 6117(4) | 1840(3) | 69(2) |
| C(9) | −3413(8) | 6578(4) | 2187(3) | 77(2) |
| C(10) | −2001(9) | 4601(5) | 870(3) | 85(3) |
| C(11) | −1871(15) | 4487(7) | 101(3) | 167(6) |
| C(12) | −1510(2) | 4009(8) | −168(5) | 343(17) |
| C(13) | −4531(8) | 2670(4) | 1706(3) | 66(2) |
| C(14) | −5897(9) | 1934(5) | 1252(3) | 130(4) |
| C(15) | −3690(9) | 3426(4) | 2525(3) | 86(3) |
| C(20) | 1740(10) | −307(5) | 1327(3) | 74(2) |
| C(21) | 2796(13) | −720(6) | 1214(3) | 134(4) |
| C(22) | 2816(18) | −1086(7) | 821(4) | 174(6) |
| C(23) | 1750(2) | −1045(9) | 545(5) | 167(7) |
| C(24) | 715(15) | −620(10) | 641(4) | 179(8) |
| C(25) | 690(10) | −253(6) | 1045(4) | 120(4) |
| C(1') | −1896(9) | 2906(4) | 1121(2) | 61(2) |
| C(2') | −1990(10) | 2444(5) | 769(3) | 94(3) |
| C(3') | −984(15) | 1925(6) | 672(4) | 127(4) |
| C(4') | 62(16) | 1900(7) | 941(5) | 143(5) |
| C(5') | 238(10) | 2367(6) | 1281(4) | 113(3) |
| C(6') | −726(9) | 2863(4) | 1372(3) | 84(3) |

The properties of crystalline lattice of the known prior art amlodipine besylate anhydrate: orthorhombic, space group Pbca, unit cell dimensions: a=10.1058(7), b=18.3269(13), c=30.4746(14) Å, α=β=γ=90°

V=5644.1(6) Å$^3$, Z=8.

EXAMPLE 9

Crystals of amlodipine besylate dihydrate suitable for X-ray diffraction studies were obtained as described in example 6(a). A single crystal was mounted in air on a glass fiber. Intensity data were collected at room temperature. An Enraf-Nonius CAD4 single-crystal diffractometer was used, CuKα radiation, ω-2θ scan mode. Unit cell dimensions were determined from the angular settings of 25 reflections. Intensity data were corrected for Lorentz and polarization effects. Semi-empirical absorption correction (ψ-scans) was applied. Basic data obtained by the measurement are listed in the Table 2.

TABLE 2

Atomic coordinates (×10⁴) and equivalent isotropic displacement parameters ($Å^2 \times 10^3$). $U_{eq}$ is defined as one third of the trace of the orthogonalized $U_{ij}$ tensor.

| | x | y | z | $U_{eq}$ |
|---|---|---|---|---|
| Cl(1) | 1448(1) | −3239(1) | 4809(1) | 72(1) |
| S(1) | 1760(1) | 2348(1) | 277(1) | 45(1) |
| N(1) | −1235(1) | −3181(2) | 1925(1) | 40(1) |
| N(2) | −3834(1) | −2898(2) | 260(1) | 45(1) |
| O(1) | −2667(1) | −2024(2) | 1569(1) | 49(1) |
| O(2) | −1737(1) | −1434(3) | 3784(1) | 86(1) |
| O(3) | −585(1) | −2460(3) | 4453(1) | 89(1) |
| O(4) | 651(1) | −6342(2) | 2386(1) | 62(1) |
| O(5) | 1252(1) | −5131(2) | 3385(1) | 57(1) |
| O(6) | 1026(1) | 3102(2) | 345(1) | 56(1) |
| O(7) | 1578(1) | 906(2) | 111(1) | 80(1) |
| O(8) | 2138(1) | 3038(2) | −225(1) | 67(1) |
| O(9) | 106(1) | 1926(2) | 1151(1) | 50(1) |
| O(10) | 5085(1) | 5905(2) | 963(1) | 62(1) |
| C(2) | −1432(1) | −2600(2) | 2516(1) | 39(1) |
| C(3) | −888(1) | −2703(2) | 3193(1) | 42(1) |
| C(4) | −21(1) | −3355(2) | 3316(1) | 40(1) |
| C(5) | −18(1) | −4287(2) | 2669(1) | 38(1) |
| C(6) | −586(1) | −4113(2) | 2007(1) | 37(1) |
| C(7) | −2288(1) | −1924(2) | 2333(1) | 45(1) |
| C(8) | −3467(1) | −1380(2) | 1346(1) | 45(1) |
| C(9) | −3777(1) | −1439(2) | 524(1) | 45(1) |
| C(10) | −1130(2) | −2126(3) | 3816(1) | 57(1) |
| C(11) | −783(3) | −1942(7) | 5102(2) | 142(2) |
| C(12) | −179(4) | −2083(11) | 5691(2) | 244(5) |
| C(13) | 634(1) | −5355(2) | 2775(1) | 40(1) |
| C(14) | 1938(2) | −6101(3) | 3552(2) | 64(1) |
| C(15) | −602(2) | −4859(3) | 1313(1) | 48(1) |
| C(20) | 2506(1) | 2434(2) | 1149(1) | 46(1) |
| C(21) | 2510(2) | 1387(4) | 1652(2) | 71(1) |
| C(22) | 3072(3) | 1473(6) | 2340(2) | 103(1) |
| C(23) | 3606(3) | 2586(7) | 2515(2) | 113(2) |
| C(24) | 3606(2) | 3629(6) | 2016(2) | 95(1) |
| C(25) | 3040(2) | 3559(3) | 1314(2) | 63(1) |
| C(1') | 657(1) | −2230(2) | 3439(1) | 42(1) |
| C(2') | 1322(1) | −2092(2) | 4077(1) | 51(1) |
| C(3') | 1916(2) | −1043(3) | 4155(2) | 66(1) |
| C(4') | 1864(2) | −116(3) | 3600(2) | 71(1) |
| C(5') | 1215(2) | −226(3) | 2959(2) | 63(1) |
| C(6') | 629(1) | −1274(2) | 2887(1) | 48(1) |

The properties of crystalline lattice of amlodipine besylate dihydrate: monoclinic, space group $P2_1/a$, unit cell dimensions: a=16.6291(7), b=9.5989(4), c=19.0656(6) Å, $\alpha=\gamma=90°$ $\beta=106.621(4)°$, V=2916.1(2) $Å^3$, Z=4.

EXAMPLE 10

A single crystal of amlodipine besylate monohydrate, obtained from example 6(b), was measured under the similar conditions as in Example 9. Unit cell dimensions were determined from the angular settings of 16 reflections. Basic data obtained by the measurement are listed in the Table 3. The structure of this monohydrate is somewhat unusual. A certain degree of disorder leads to a sort of supercell structure with a large number of independent positions. It is possible that this is related to the considerable difficulties which were encountered in obtaining crystals of suitable size for X-ray analysis, and leads to the very small, but pharmaceutically favorable, crystals which are usually obtained.

TABLE 3

Atomic coordinates (×10⁴) and equivalent isotropic displacement parameters ($Å^2 \times 10^3$). $U_{eq}$ is defined as one third of the trace of the orthogonalized $U_{ij}$ tensor.

| | x | y | z | $U_{eq}$ |
|---|---|---|---|---|
| N(1A) | 2463(5) | 1646(5) | 7505(2) | 59(2) |
| C(2A) | 2234(5) | 2052(5) | 7807(3) | 47(2) |
| C(3A) | 2734(5) | 2426(5) | 8013(3) | 49(2) |
| C(4A) | 3576(6) | 2364(6) | 7943(3) | 48(2) |
| C(5A) | 3738(5) | 2031(6) | 7558(3) | 47(2) |
| C(6A) | 3196(6) | 1672(6) | 7372(3) | 53(3) |
| C(7A) | 1382(6) | 1976(7) | 7874(3) | 60(3) |
| O(1A) | 962(4) | 1883(4) | 7544(2) | 60(2) |
| C(8A) | 814(7) | 2570(7) | 7359(3) | 66(3) |
| C(9A) | 332(6) | 2404(7) | 7033(3) | 64(3) |
| N(2A) | 753(5) | 1977(5) | 6742(2) | 59(2) |
| C(10A) | 2491(6) | 2850(6) | 8324(3) | 53(2) |
| O(2A) | 1885(5) | 2826(5) | 8476(2) | 79(2) |
| O(3A) | 3047(4) | 3315(4) | 8448(2) | 66(2) |
| C(11A) | 2923(8) | 3726(7) | 8788(3) | 78(3) |
| C(12A) | 3051(11) | 3256(9) | 9096(4) | 110(5) |
| C(13A) | 4484(6) | 2140(6) | 7411(3) | 56(3) |
| O(4A) | 4730(4) | 1905(5) | 7123(2) | 74(2) |
| O(5A) | 4941(4) | 2527(5) | 7632(2) | 70(2) |
| C(14A) | 5694(6) | 2703(6) | 7518(4) | 75(4) |
| C(15A) | 3284(7) | 1277(8) | 7015(3) | 74(3) |
| C(1A') | 3939(6) | 1886(7) | 8239(3) | 57(3) |
| C(2A') | 4480(7) | 2148(8) | 8484(3) | 81(4) |
| Cl(1A) | 4848(2) | 3056(3) | 8441(1) | 105(2) |
| C(3A') | 4762(9) | 1694(12) | 8755(4) | 100(5) |
| C(4A') | 4485(12) | 971(15) | 8791(4) | 128(8) |
| C(5A') | 3982(9) | 667(10) | 8551(5) | 100(5) |
| C(6A') | 3692(6) | 1130(7) | 8277(3) | 68(3) |
| Cl(6A) | 3210(6) | 640(6) | 8080(3) | 180(4) |
| N(1B) | 7373(5) | 1494(5) | 5625(2) | 57(2) |
| C(2B) | 6966(5) | 1733(6) | 5336(2) | 48(2) |
| C(3B) | 6572(5) | 1236(5) | 5127(2) | 45(2) |
| C(4B) | 6616(6) | 371(6) | 5198(2) | 55(3) |
| C(5B) | 6938(6) | 215(6) | 5568(3) | 48(2) |
| C(6B) | 7324(6) | 751(7) | 5760(3) | 57(3) |
| C(7B) | 7014(8) | 2589(6) | 5265(3) | 67(3) |
| O(1B) | 7133(4) | 3012(4) | 5596(2) | 61(2) |
| C(8B) | 6449(7) | 3176(7) | 5786(3) | 67(3) |
| C(9B) | 6606(7) | 3648(7) | 6100(3) | 69(3) |
| N(2B) | 6999(5) | 3225(5) | 6398(2) | 62(2) |
| C(10B) | 6139(6) | 1494(7) | 4815(3) | 56(3) |
| O(2B) | 6160(5) | 2112(5) | 4665(2) | 74(2) |
| O(3B) | 5645(4) | 947(4) | 4708(2) | 64(2) |
| C(11B) | 5215(6) | 1078(8) | 4371(3) | 69(3) |
| C(12B) | 5712(8) | 953(8) | 4050(3) | 87(4) |
| C(13B) | 6836(6) | −561(7) | 5713(3) | 59(3) |
| O(4B) | 7081(5) | −804(5) | 6003(2) | 79(2) |
| O(5B) | 6423(4) | −989(4) | 5495(2) | 72(2) |
| C(14B) | 6213(8) | −1734(7) | 5618(5) | 100(5) |
| C(15B) | 7735(8) | 637(7) | 6114(3) | 77(3) |
| C(1B') | 7044(7) | −3(6) | 4880(3) | 58(3) |
| C(2B') | 6737(9) | −532(8) | 4644(3) | 87(4) |
| Cl(1B) | 5819(3) | −857(2) | 4672(1) | 117(2) |
| C(3B') | 7135(17) | −809(13) | 4363(5) | 139(8) |
| C(4B') | 7890(2) | −595(14) | 4308(5) | 153(12) |
| C(5B') | 8203(13) | −120(13) | 4539(6) | 138(9) |
| C(6B') | 7788(8) | 199(8) | 4829(4) | 82(4) |
| Cl(6B) | 8282(8) | 711(8) | 5003(4) | 150(4) |
| N(1C) | 8048(5) | 5856(5) | 5630(2) | 55(2) |
| C(2C) | 8273(5) | 5468(5) | 5319(3) | 53(2) |
| C(3C) | 7763(5) | 5120(6) | 5120(3) | 50(2) |
| C(4C) | 6909(6) | 5137(7) | 5197(3) | 54(3) |
| C(5C) | 6768(6) | 5464(6) | 5572(3) | 50(2) |
| C(6C) | 7323(6) | 5816(6) | 5761(3) | 55(3) |
| C(7C) | 9110(6) | 5516(7) | 5256(3) | 63(3) |
| O(1C) | 9544(4) | 5621(4) | 5573(2) | 59(2) |
| C(8C) | 9662(7) | 4903(7) | 5756(3) | 65(3) |
| C(9C) | 10154(6) | 5042(7) | 6078(3) | 70(3) |
| N(2C) | 9769(5) | 5468(5) | 6363(2) | 61(2) |
| C(10C) | 7993(7) | 4728(7) | 4776(3) | 67(3) |
| O(2C) | 8569(5) | 4823(5) | 4613(2) | 84(3) |
| O(3C) | 7454(4) | 4215(5) | 4671(2) | 74(2) |
| C(11C) | 7556(9) | 3831(9) | 4332(4) | 97(5) |

TABLE 3-continued

Atomic coordinates (×10⁴) and equivalent isotropic displacement parameters ($\text{Å}^2 \times 10^3$). $U_{eq}$ is defined as one third of the trace of the orthogonalized $U_{ij}$ tensor.

| | x | y | z | $U_{eq}$ |
|---|---|---|---|---|
| C(12C) | 7237(10) | 4321(14) | 4022(4) | 133(7) |
| C(13C) | 6013(6) | 5358(6) | 5734(3) | 58(3) |
| O(4C) | 5788(5) | 5590(6) | 6014(2) | 82(2) |
| O(5C) | 5584(4) | 4931(5) | 5509(3) | 78(2) |
| C(14C) | 4830(8) | 4738(9) | 5652(5) | 103(5) |
| C(15C) | 7232(8) | 6177(8) | 6132(3) | 83(4) |
| C(1C') | 6524(6) | 5621(8) | 4911(3) | 66(3) |
| C(2C') | 5954(8) | 5330(12) | 4672(4) | 106(6) |
| Cl(1C) | 5613(2) | 4459(4) | 4692(2) | 130(3) |
| C(3C') | 5685(12) | 5832(18) | 4399(4) | 142(10) |
| C(4C') | 5911(16) | 6560(2) | 4358(7) | 168(15) |
| C(5C') | 6422(14) | 6800(13) | 4589(6) | 147(10) |
| C(6C') | 6732(11) | 6364(12) | 4856(4) | 95(5) |
| Cl(6C) | 7187(18) | 6780(2) | 4957(10) | 118(13) |
| N(1D) | 8156(5) | 883(5) | 7507(2) | 57(2) |
| C(2D) | 8543(5) | 652(6) | 7812(3) | 52(2) |
| C(3D) | 8908(5) | 1143(6) | 8017(3) | 54(2) |
| C(4D) | 8874(5) | 2006(5) | 7949(3) | 46(2) |
| C(5D) | 8519(6) | 2167(7) | 7575(3) | 58(3) |
| C(6D) | 8150(6) | 1629(7) | 7377(3) | 54(3) |
| C(7D) | 8497(6) | −206(6) | 7872(3) | 62(3) |
| O(1D) | 8405(4) | −620(4) | 7548(2) | 57(2) |
| C(8D) | 9100(5) | −708(7) | 7358(3) | 66(3) |
| C(9D) | 8963(7) | −1211(6) | 7032(3) | 67(3) |
| N(2D) | 8531(5) | −788(5) | 6751(2) | 61(2) |
| C(10D) | 9322(7) | 919(7) | 8350(3) | 63(3) |
| O(2D) | 9211(5) | 332(5) | 8517(2) | 82(2) |
| O(3D) | 9823(5) | 1441(5) | 8455(2) | 82(2) |
| C(11D) | 10182(10) | 1283(9) | 8792(4) | 117(6) |
| C(12D) | 10280(2) | 1954(12) | 8990(6) | 242(18) |
| C(13D) | 8629(6) | 2922(6) | 7416(4) | 64(3) |
| O(4D) | 8369(6) | 3171(5) | 7141(2) | 86(3) |
| O(5D) | 9066(5) | 3355(4) | 7634(3) | 82(2) |
| C(14D) | 9255(8) | 4134(8) | 7508(5) | 98(5) |
| C(15D) | 7777(8) | 1703(8) | 7023(3) | 81(4) |
| C(1D') | 8483(6) | 2434(6) | 8259(3) | 64(3) |
| C(2D') | 7763(7) | 2291(8) | 8393(4) | 100(5) |
| Cl(1D) | 7184(2) | 1648(3) | 8176(1) | 87(2) |
| C(3D') | 7424(10) | 2668(10) | 8690(4) | 103(5) |
| C(4D') | 7857(10) | 3190(10) | 8856(5) | 105(5) |
| C(5D') | 8570(10) | 3358(9) | 8748(4) | 109(5) |
| C(6D') | 8891(9) | 3005(7) | 8459(3) | 91(4) |
| Cl(6D) | 9628(10) | 3340(10) | 8342(5) | 117(6) |
| S(1A) | 9075(2) | 7622(2) | 6095(1) | 57(1) |
| O(7A) | 9761(5) | 7974(6) | 6218(3) | 86(3) |
| O(8A) | 9055(5) | 6789(4) | 6152(2) | 69(2) |
| O(9A) | 8427(5) | 7975(5) | 6273(2) | 76(2) |
| C(20A) | 8973(5) | 7765(6) | 5638(3) | 52(2) |
| C(21A) | 8355(8) | 8121(9) | 5500(4) | 89(4) |
| C(22A) | 8275(10) | 8236(11) | 5137(4) | 111(6) |
| C(23A) | 8845(11) | 8002(9) | 4897(4) | 103(5) |
| C(24A) | 9479(9) | 7684(9) | 5028(4) | 88(4) |
| C(25A) | 9538(6) | 7542(7) | 5398(4) | 73(3) |
| S(1B) | 1452(2) | 9846(2) | 7016(1) | 56(1) |
| O(7B) | 747(5) | 9513(6) | 6902(2) | 83(3) |
| O(8B) | 1474(5) | 10675(4) | 6984(2) | 69(2) |
| O(9B) | 2116(4) | 9487(5) | 6869(2) | 70(2) |
| C(20B) | 1508(6) | 9670(6) | 7500(3) | 55(3) |
| C(21B) | 2118(6) | 9277(7) | 7645(3) | 66(3) |
| C(22B) | 2160(9) | 9156(9) | 8014(4) | 93(4) |
| C(23B) | 1600(9) | 9415(8) | 8229(4) | 88(4) |
| C(24B) | 1006(8) | 9809(8) | 8087(4) | 86(4) |
| C(25B) | 960(7) | 9939(7) | 7729(3) | 72(3) |
| S(1C) | 9114(2) | 2541(2) | 6106(1) | 56(1) |
| O(7C) | 9514(5) | 1885(5) | 6273(2) | 76(2) |
| O(8C) | 9430(5) | 3250(5) | 6236(2) | 86(3) |
| O(9C) | 8304(4) | 2476(5) | 6169(2) | 72(2) |
| C(20C) | 9243(6) | 2485(6) | 5641(3) | 59(3) |
| C(21C) | 8976(7) | 3055(7) | 5421(4) | 69(3) |
| C(22C) | 9108(9) | 3010(10) | 5049(4) | 100(5) |
| C(23C) | 9468(8) | 2372(10) | 4912(4) | 90(4) |
| C(24C) | 9722(9) | 1833(11) | 5125(4) | 105(5) |
| C(25C) | 9643(7) | 1877(8) | 5491(4) | 79(4) |
| S(1D) | 6376(2) | 9885(2) | 6983(1) | 55(1) |
| O(7D) | 6036(4) | 10560(4) | 6821(2) | 66(2) |
| O(8D) | 6038(6) | 9174(5) | 6873(3) | 92(3) |
| O(9D) | 7189(4) | 9877(5) | 6961(2) | 73(2) |
| C(20D) | 6192(5) | 9986(6) | 7456(3) | 52(2) |
| C(21D) | 6465(7) | 9475(8) | 7703(4) | 75(3) |
| C(22D) | 6350(8) | 9560(8) | 8066(3) | 80(4) |
| C(23D) | 5912(10) | 10140(9) | 8191(4) | 99(5) |
| C(24D) | 5606(8) | 10666(7) | 7944(4) | 83(4) |
| C(25D) | 5759(7) | 10580(7) | 7582(3) | 72(3) |
| O(31) | 1912(6) | 7011(8) | 1590(4) | 112(4) |
| H(31A) | 2195(19) | 7150(2) | 1682(10) | 167 |
| H(31B) | 1432(15) | 7167(15) | 1290(7) | 167 |
| O(32) | 3552(6) | 467(6) | 1521(4) | 113(4) |
| H(32A) | 3830(17) | 821(17) | 1534(8) | 169 |
| H(32B) | 3040(15) | 293(15) | 1834(7) | 169 |
| O(33) | 1002(5) | 2942(6) | 1528(3) | 101(3) |
| O(34) | 4539(6) | 4592(6) | 1618(3) | 101(3) |

The properties of crystalline lattice of amlodipine besylate monohydrate:

Monoclinic, Space group Cc

Unit cell dimensions: a=17.689(2) Å, b=17.533(7) Å, c=36.843(11) Å, α=γ=90°. β=90.182(17)°.

V=11426(6) Å³

Z=16

EXAMPLE 11

Pharmaceutical tablets comprising amlodipine besylate monohydrate are prepared by direct compression. The tablet compositions, which provide to 2.5 mg of amlodipine free base, are as follows:

| Composition of tablets (equivalent to 2.5 mg of amlodipine) | | | | |
|---|---|---|---|---|
| Amlodipine besylate monohydrate | 3.57 mg | 3.57 mg | 3.57 mg | 3.57 mg |
| CaHPO4 anhydrous (DiCafos A) | — | 31.5 mg | — | — |
| CaHPO4 dihydrate (Ditab) | 31.5 mg | — | — | 31.5 mg |
| Microcryst. cellulose PH102 | 61.68 mg | — | 93.53 mg | 61.53 mg |
| Microcryst. cellulose PH112 | — | 61.68 mg | — | — |
| Sodium starch glycollate | 2.0 mg | 2.0 mg | 2.0 mg | 2.0 mg |
| Magnesium stearate | 1.0 mg | 1.0 mg | 0.5 mg | 1.0 mg |
| Iron oxide dye | 0.25 mg | 0.25 mg | 0.40 mg | 0.40 mg |

The disclosure in each of the patents mentioned above is incorporated herein by reference in their entirety. The invention having been described, it will be readily apparent to those skilled in the art that further changes and modifications in actual implementation of the concepts and embodiments described herein can easily be made or may be learned by practice of the invention, without departing from the spirit and scope of the invention as defined by the following claims.

We claim:

1. A crystalline amlodipine besylate monohydrate.

2. The amlodipine besylate monohydrate according to claim 1, having a melting point on differential scanning calorimetry (DSC) within the range of 92–104°C.

3. The amlodipine besylate monohydrate according to claim 1, having a purity of at least 99%.

4. The amlodipine besylate monohydrate according to claim 1, which exhibits an IR spetra corresponding to FIG. 6.

5. The amlodipine besylate monohydrate according to claim 1, which exhibits an x-ray powder diffraction pattern corresponding to FIG. 9C.

6. The amlodipine besylate monohydrate according to claim 1, which is in the form of particles having an average particle size of 100 microns or less.

7. The amlodipine besylate monohydrate according to claim 6, wherein said particles have an average particle size of 50 microns or less.

8. The amlodipine besylate monohydrate according to claim 7, which is in the form of particles having an average particle size of 10 microns or less.

9. A pharmaceutical composition comprising 1 to 20 mg of crystalline amlodipine besylate monohydrate, microcrystalline cellulose, sodium starch glycollate, and magnesium stearate.

10. The pharmaceutical composition according to claim 9, which is in the form of a tablet.

11. The pharmaceutical composition according to claim 10, which consists essentially of crystalline amlodipine besylate monohydrate, microcrystalline cellulose, sodium starch glycollate, and magnesium stearate.

12. The pharmaceutical composition according to claim 11, wherein said crystalline amlodipine besylate monohydrate exhibits an JR spectra corresponding to FIG. 6.

13. The pharmaceutical composition according to claim 11, wherein said crystalline amlodipine besylate monohydrate exhibits an x-ray powder diffraction pattern corresponding to FIG. 9C.

14. The pharmaceutical composition according to claim 11, wherein said crystalline amlodipine besylate monohydrate are particles having an average particle size of 50 microns or less.

15. The pharmaceutical composition according to claim 11, wherein said crystalline amlodipine besylate monohydrate are particles having an average particle size of 10 microns or less.

* * * * *